United States Patent
Miller

(10) Patent No.: US 10,477,941 B2
(45) Date of Patent: Nov. 19, 2019

(54) VOLATILE LIQUID APPLICATOR SYSTEMS AND FUME-FILTERING APPARATUSES

(71) Applicant: L'Oreal, Paris (FR)

(72) Inventor: Zane Bowman Allen Miller, Seattle, WA (US)

(73) Assignee: L'Oreal, Paris (FR)

( * ) Notice: Subject to any disclaimer, the term of this patent is extended or adjusted under 35 U.S.C. 154(b) by 238 days.

(21) Appl. No.: 15/581,905

(22) Filed: Apr. 28, 2017

(65) Prior Publication Data

US 2018/0310689 A1  Nov. 1, 2018

(51) Int. Cl.
| | | |
|---|---|---|
| *A46B 11/00* | (2006.01) | |
| *A45D 34/04* | (2006.01) | |
| *A45D 29/00* | (2006.01) | |
| *A61L 9/12* | (2006.01) | |
| *B01D 53/04* | (2006.01) | |

(52) U.S. Cl.
CPC ........... *A45D 34/042* (2013.01); *A45D 29/00* (2013.01); *A45D 34/045* (2013.01); *A61L 9/122* (2013.01); *B01D 53/0407* (2013.01); *A45D 2200/20* (2013.01); *B01D 2253/102* (2013.01); *B01D 2253/108* (2013.01); *B01D 2253/112* (2013.01); *B01D 2257/708* (2013.01); *B01D 2258/06* (2013.01)

(58) Field of Classification Search
CPC .. A45D 34/042; A45D 34/045; A45D 40/262; A45D 40/265
See application file for complete search history.

(56) References Cited

U.S. PATENT DOCUMENTS

| | | |
|---|---|---|
| 4,062,274 A | 12/1977 | Knab |
| 5,795,219 A | 8/1998 | Bloom |
| 2003/0200977 A1* | 10/2003 | Hu .......... A45D 29/20 132/73 |
| 2007/0238404 A1* | 10/2007 | Park ........ A45D 29/18 454/56 |
| 2010/0303532 A1 | 12/2010 | Brunozzi |
| 2013/0213424 A1* | 8/2013 | Kim ........ A45D 29/11 132/73.6 |
| 2017/0354235 A1* | 12/2017 | Miller ....... A45D 34/045 |

FOREIGN PATENT DOCUMENTS

| | | | |
|---|---|---|---|
| EP | 443207 | 8/1991 | |
| KR | 2020110002647 | * 3/2011 | ............. A45D 34/04 |

* cited by examiner

*Primary Examiner* — Jennifer C Chiang
(74) *Attorney, Agent, or Firm* — Christensen O'Connor Johnson Kindness PLLC

(57) ABSTRACT

Volatile liquid applicator systems and fume-filtering apparatuses and related method of use are described.

19 Claims, 9 Drawing Sheets

VOLATILE LIQUID APPLICATOR SYSTEMS AND FUME-FILTERING APPARATUSES

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides a volatile liquid applicator system generally including a body structure including a volatile liquid applicator and an air flow body including a filter; and an electrical fan assembly associated with the air flow body, the electrical fan assembly configured to direct fumes associated with a volatile liquid away from a portion of the volatile liquid applicator and across the air filter.

In another aspect, the present disclosure provides a fume-filtering apparatus generally including an air flow body including a filter, the air flow body configured to couple with a body structure of a volatile liquid applicator; and an electrical fan assembly associated with the air flow body, the electrical fan assembly configured to direct fumes associated with a volatile liquid away from a portion of the volatile liquid applicator and across the filter.

In accordance with any of the embodiments disclosed herein, the air flow body may be configured to assist in drying based on redirecting air direction.

In accordance with any of the embodiments disclosed herein, the air flow body may include a passageway configured to allow passage of the fumes through the air flow body and across the filter. In accordance with any of the embodiments disclosed herein, the passageway is one of a plurality of passageways configured to allow passage of the fumes through the air flow body and across the filter.

In accordance with any of the embodiments disclosed herein, the electrical fan assembly may include a fan structure chosen from an inductive fan, an axial-flow fan, a centrifugal fan, a cross-flow fan, and combinations thereof.

In accordance with any of the embodiments disclosed herein, the filter may be configured to absorb a volatile organic compound. In accordance with any of the embodiments disclosed herein, the filter may be configured to adsorb a compound chosen from ethanol, propanol, isopropanol, ethyl acetate, propyl acetate, butyl acetate, toluene, xylene, formalin, formaldehyde, benzophenone, dibutylphthalate, and combinations thereof.

In accordance with any of the embodiments disclosed herein, the filter may include an adsorbent chosen from activated carbon, potassium permanganate, zeolites, and combinations thereof.

In accordance with any of the embodiments disclosed herein, the filter may be configured to be removably affixed to the air flow body.

In accordance with any of the embodiments disclosed herein, the volatile liquid applicator system includes a container for containing a volatile liquid, wherein the container may be configured to removably couple with the body structure. In accordance with any of the embodiments disclosed herein, the container for containing a volatile liquid may include a volatile liquid. In accordance with any of the embodiments disclosed herein, the volatile liquid may be chosen from nail polish, hair dye, and combinations thereof.

In accordance with any of the embodiments disclosed herein, the fume-filtering apparatus may include a coupling interface configured to couple the body structure to the air flow body. In accordance with any of the embodiments disclosed herein, the coupling interface may include a magnet configured to couple the air flow body to a ferromagnetic portion of the body structure. In accordance with any of the embodiments disclosed herein, the magnet may be one of a plurality of magnets, and wherein the air flow body may be configured to maintain an orientation about a rotationally-symmetrical axis of the body structure. In accordance with any of the embodiments disclosed herein, the coupling interface may be configured to frictionally couple the air flow body to the body structure. In accordance with any of the embodiments disclosed herein, the coupling interface may include an opening in the air flow body configured to receive at least a portion of the volatile liquid applicator, and wherein the coupling interface may include an adhesive material chosen from silicon rubber, semi-permanent adhesive, removable adhesive, tacky clay, and combinations thereof disposed on at least a portion of an inner perimeter defined by the opening. In accordance with any of the embodiments disclosed herein, the coupling interface may include a coupling structure selected from the group consisting of a snap fit, a snap collar, and combinations thereof.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The present disclosure relates generally to volatile liquid applicator systems and fume-filtering apparatuses and related methods of use. Generally described, volatile liquid applicators typically include a brush or other end effector for applying a volatile liquid to a surface. Examples of such volatile liquid applicators include nail polish brushes, hair dye applicators, and the like.

Volatile compounds, such as solvents, present in personal care products evaporate creating fumes. In currently available volatile liquid applicators, volatile fumes are generated when a user applies a material containing a volatile liquid with an applicator. Such fumes frequently contain chemicals that are unpleasant, dangerous, and/or unhealthy for a user and should be contained.

To that end, the following discussion provides examples of volatile liquid applicator systems that have a filter and a fan assembly configured to direct fumes associated with a volatile liquid across the filter. As will be described in more detail below, the volatile liquid applicator systems are configured to assist in drying based on redirecting air direction. In that regard, the filter is configured to adsorb one or more volatile compound associated with the fumes.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1:
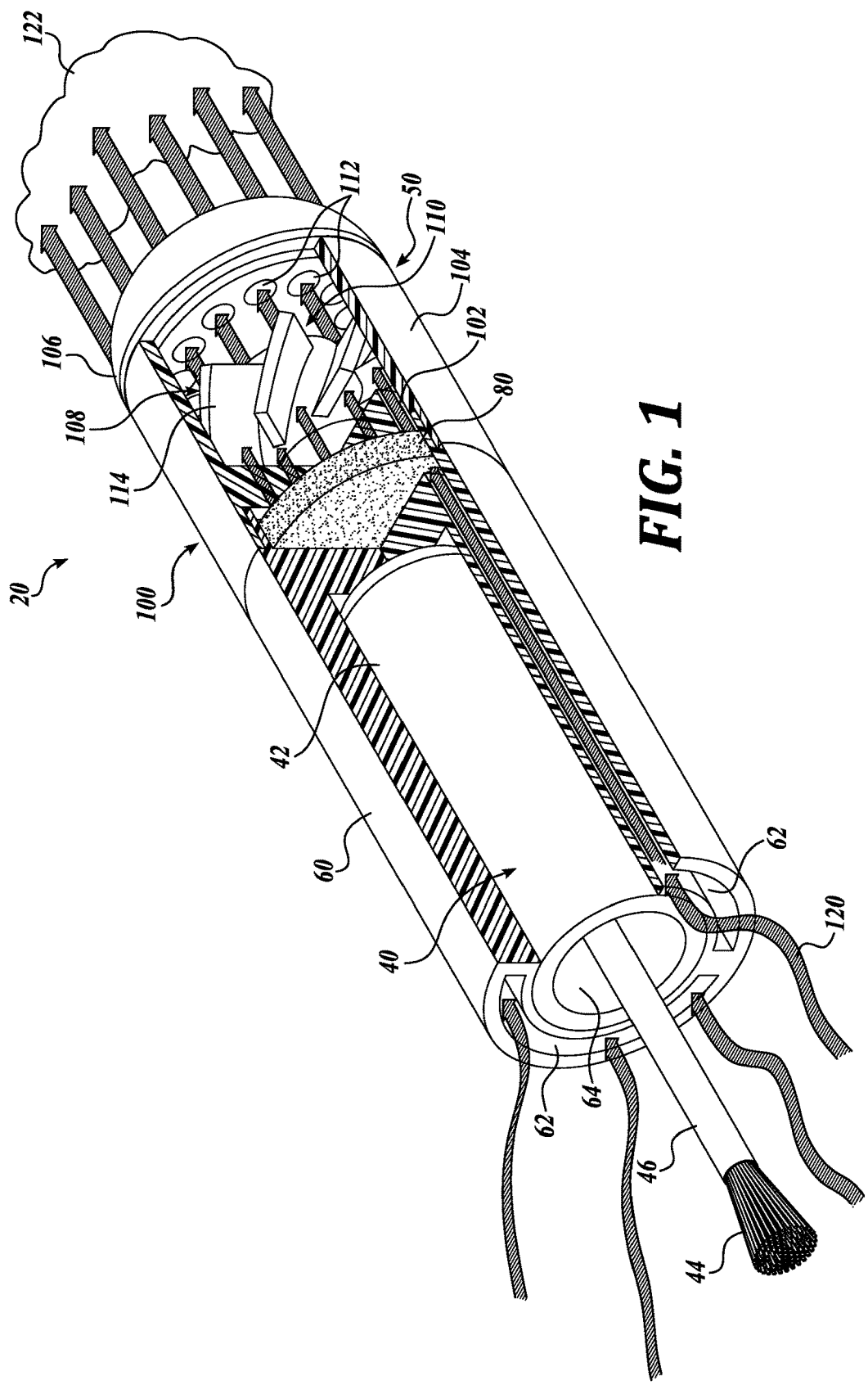
FIG. 1 is a perspective view in partial cross-section of a representative embodiment of a volatile liquid applicator system in accordance with an aspect of the disclosure.
Figure 2:
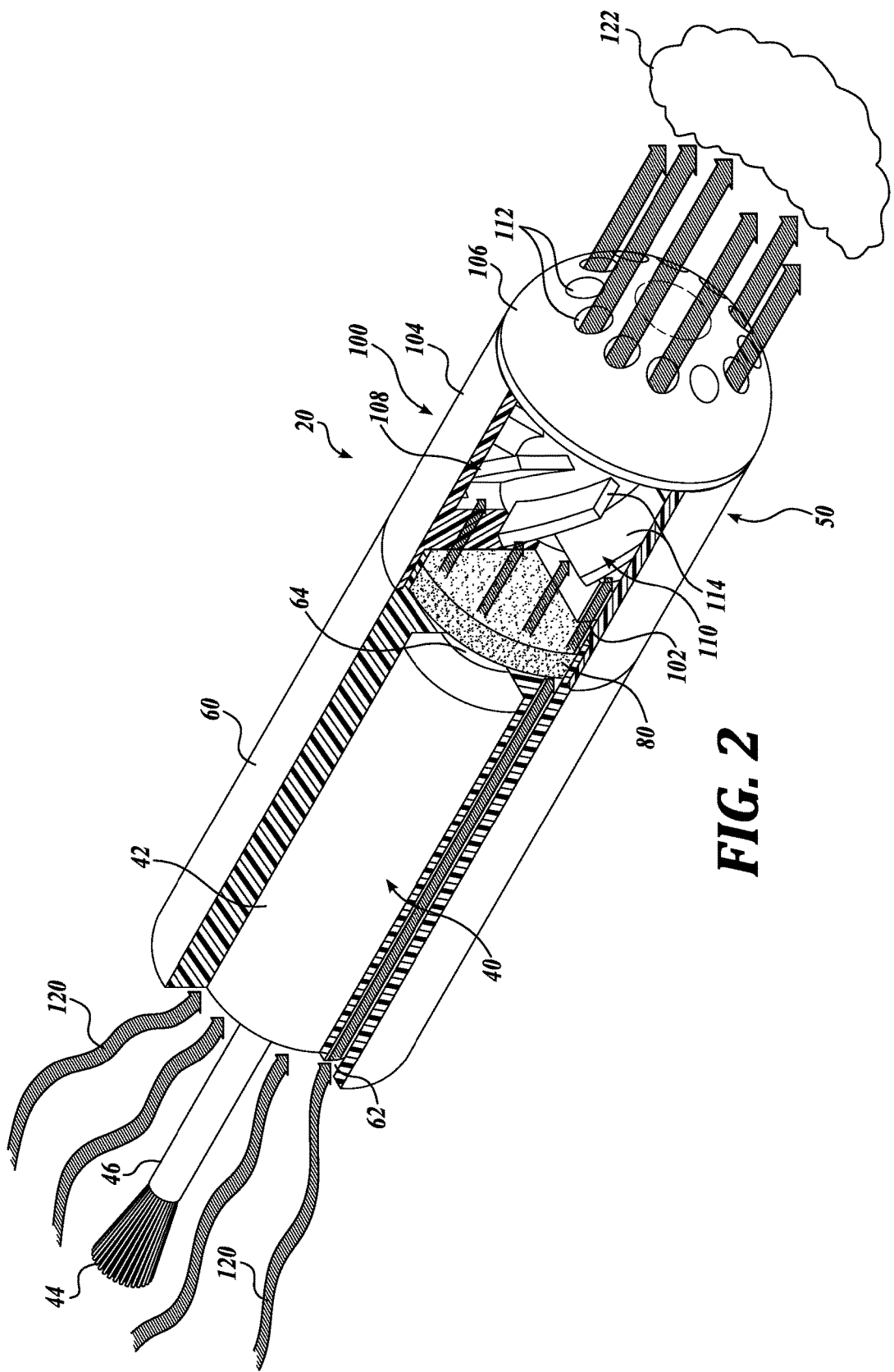
FIG. 2 is another perspective view in partial cross-section of the volatile liquid applicator system of FIG. 1.

FIGS. 1 and 2 illustrate a representative volatile liquid applicator system 20, which includes a volatile liquid applicator 40 and a fume-directing assembly 50. As shown in FIGS. 1 and 2, the volatile liquid applicator 40 includes a body structure, such as a handle or cap 42, an applicator end 44, shown as a nail polish brush, and a shaft 46 connecting the brush 44 and the handle or cap 42. The system 20 also includes the fume-directing assembly 50 that comprises an air flow body 60 and an electrical fan assembly 100 configured to direct fumes 120 associated with a volatile liquid carried by the applicator end 44 away from the volatile liquid applicator 40 and across a filter 80. As will be described in more detail below, by moving the fumes 120 across the filter 80 components of those fumes, such as volatile organic and other dangerous and/or harmful compounds, are adsorbed onto the filter 80, thereby removing them from the environment of a user.

While brushes are illustrated and described herein, other embodiments may employ other end effectors, such as applicators and the like. Brushes of any size and composition can be used. Exemplary brushes include nail polish brushes. Exemplary applicators include hair dye applicators.

Figure 5:
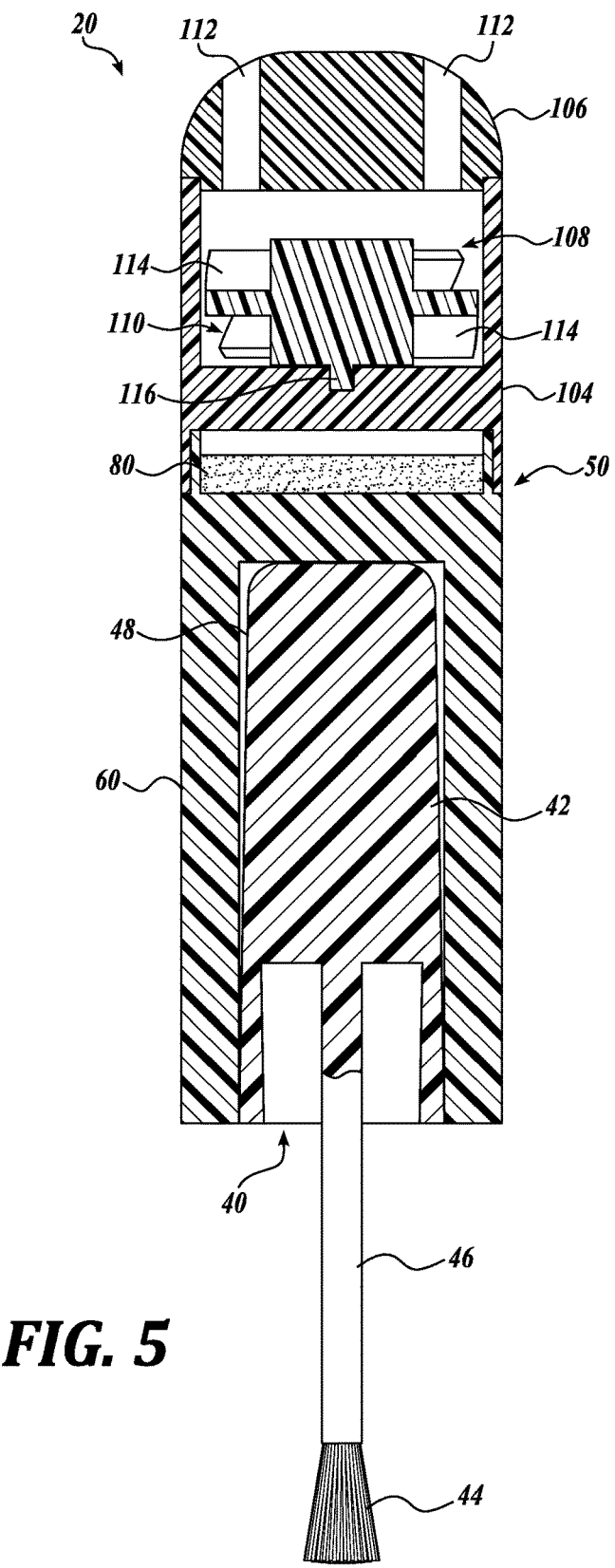
FIG. 5 is a cross-section view of the volatile liquid applicator system of FIG. 1.
Figure 6:
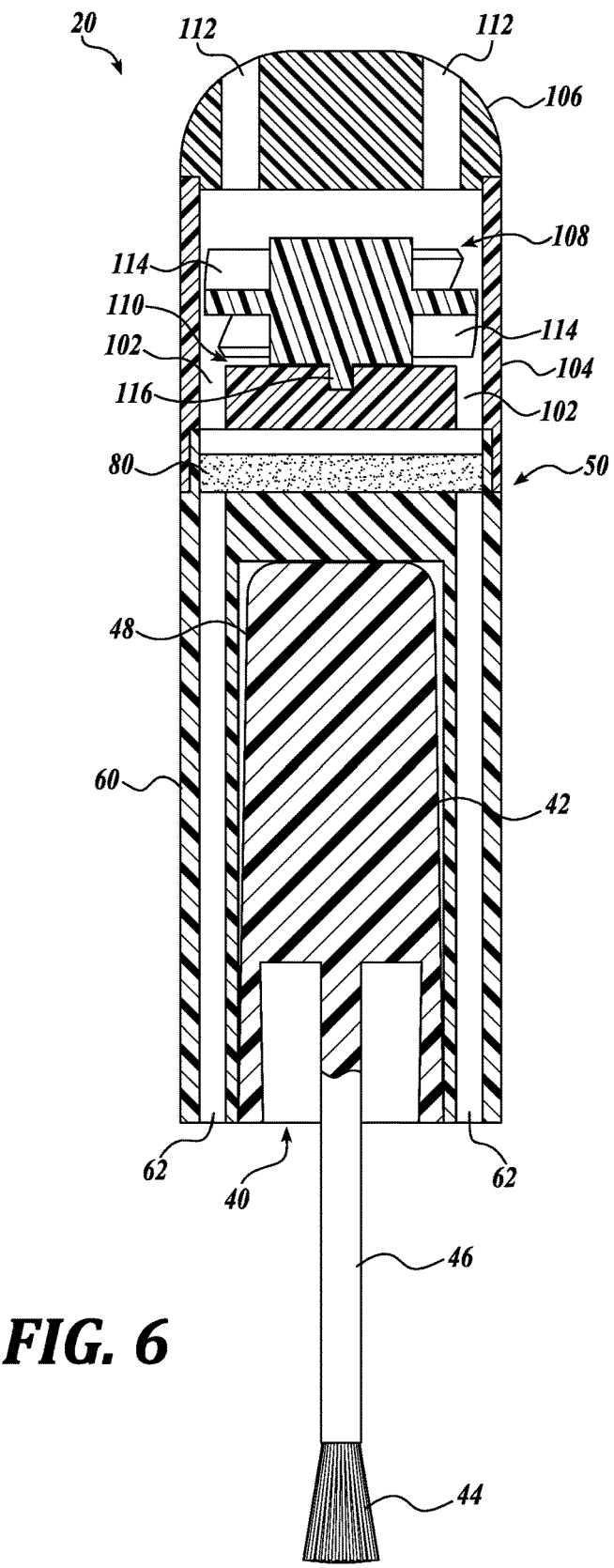
FIG. 6 is another cross-section view of the volatile liquid applicator system of FIG. 1.

Turning now to FIGS. 1-6, the components of the fume-directing assembly 50 will be described in more detail. As shown in FIGS. 2 and 6, the air flow body 60 is configured to assist in drying based on redirecting air direction. Towards that end, in some embodiments, the volatile liquid applicator system 20 includes one or more passageways configured to allow passage of fumes 120 associated with a volatile liquid applicator 40 across the filter 80. As shown in FIGS. 2, 5 and 6, the air flow body 60 can include one or more passageways 62 configured to allow passage of fumes 120 (See FIG. 2) associated with the applicator 40. In certain embodiments, such passageways 62 extend through at least a portion of the air flow body 60 from a position adjacent to the volatile liquid applicator 42 to a position adjacent to the filter 80. In the embodiment shown in FIGS. 1 and 2, the air flow body 60 is generally tubular, with the one or more passageways 62 disposed in the wall thereof. As will be described in more detail below, the tubular structure of the air flow body 60 defines a socket or bore for receiving the handle or cap 42 of the volatile liquid applicator 40.

In an embodiment, the electrical fan assembly 100 also includes one or more passageways 102 disposed in, for example, an electrical fan assembly housing 104. In certain embodiments, such passageways 102 extend through at least a portion of the electrical fan assembly 100 from a position adjacent to the filter 80 and to a position adjacent to a cap 106. The electrical fan assembly 100 can further include a cavity 110 configured to house the electrical fan 108, through which fumes 120 are directed by the electrical fan 108.

Still referring to FIGS. 2, 5, and 6, the electrical fan assembly 100 includes an electrical fan 108 operatively mounted within a cavity 110 defined by the electrical fan assembly housing 106. In certain embodiments, the cap 106 is configured to secure a portion of the electrical fan assembly 100, such as the electrical fan 108, in place. In certain embodiments, the cap 106 includes one or more passageways 112 configured to allow air flow through the electrical fan assembly 100 and out into the environment. As such, the passageways 102 are coupled in fluid communication with the passageways 112 via cavity 110.

Figure 3:
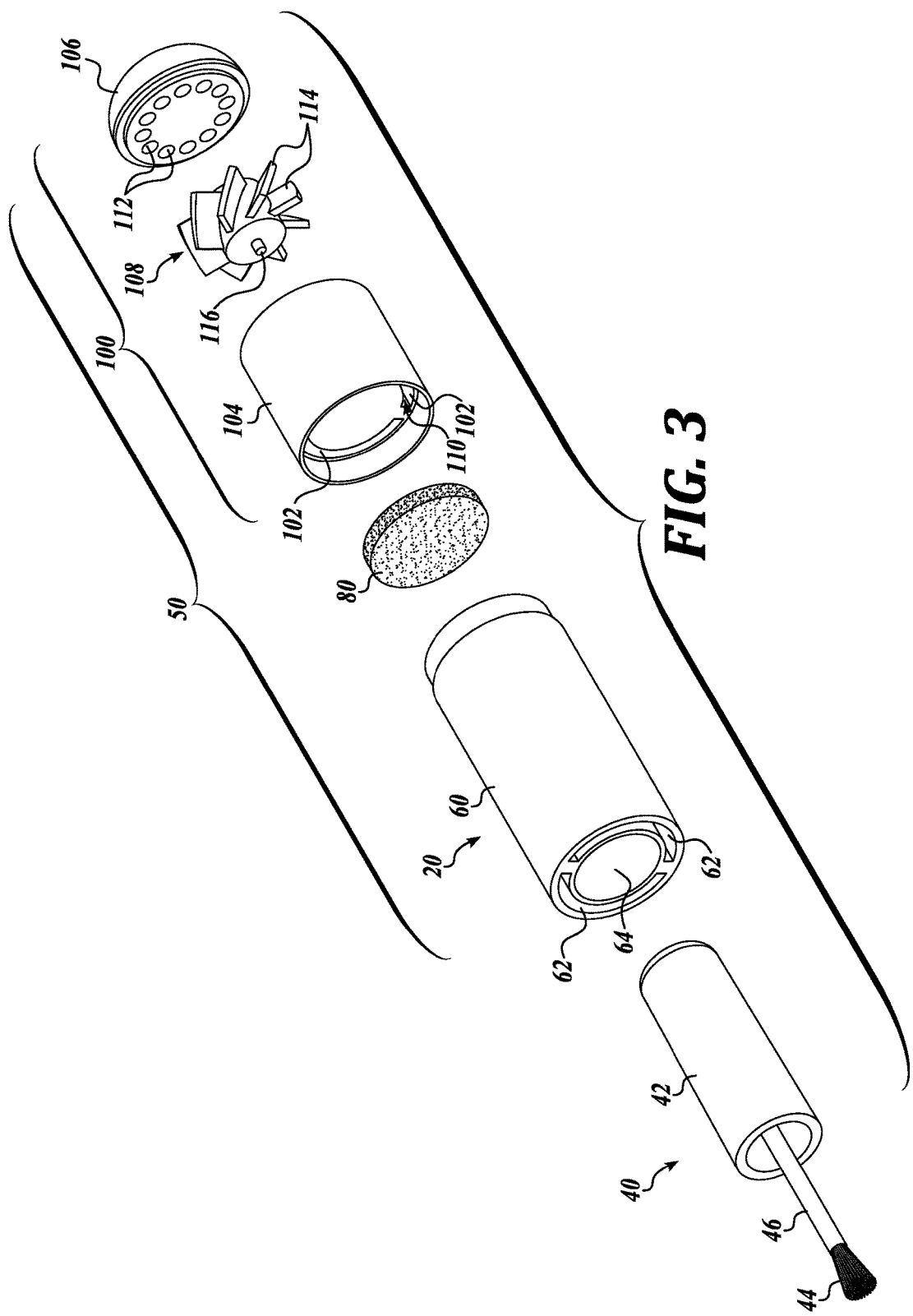
FIG. 3 is an exploded, bottom perspective view of the volatile liquid applicator system of FIG. 1.
Figure 4:
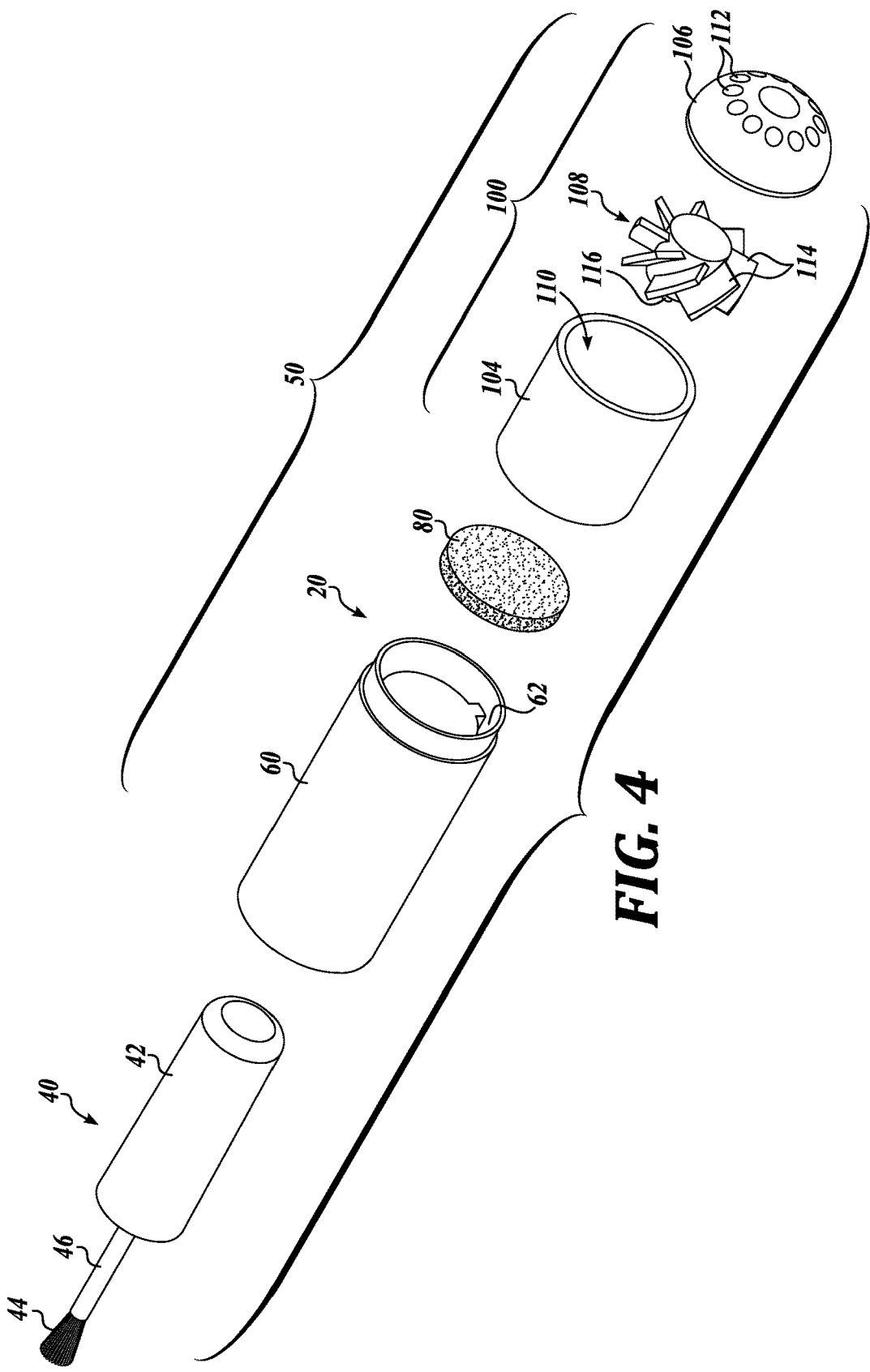
FIG. 4 is an exploded, top perspective view of the volatile liquid applicator system of FIG. 1.

The electrical fan assembly 100 is configured to direct fumes associated with a volatile liquid away from the volatile liquid applicator and across the filter 80. In that regard, the electrical fan assembly 100 includes an electrical fan 108. The electrical fan 108 can be any fan configured to direct air flow. In an embodiment, the electrical fan 108 is one of an inductive fan, an axial-flow fan, a centrifugal fan, and a cross-flow fan. In an embodiment, the electrical fan is configured to induce air flow through electrostatic forces linked to corona discharge, or "ionic wind". In another embodiment, the motor can be a venturi tube or the like. Referring to FIGS. 2 and 3, an axial flow fan 108 is illustrated. The fan 108 has a plurality of fan blades 114 that force air to move parallel to the shaft 116 about which the plurality of blades 114 rotate, thereby directing air flow.

As shown in FIG. 1, the air flow body 60 is disposed between the applicator 40 and the electrical fan 108. In such an embodiment, the electrical fan 108 is configured to draw air through the air flow body 60 and across the filter 80. In another embodiment, the electrical fan 108 is disposed between the volatile liquid applicator 40 and the air flow body 60 and configured to push air from the volatile liquid applicator 40 into the air flow body 60 and across the filter 80.

Figure 10:
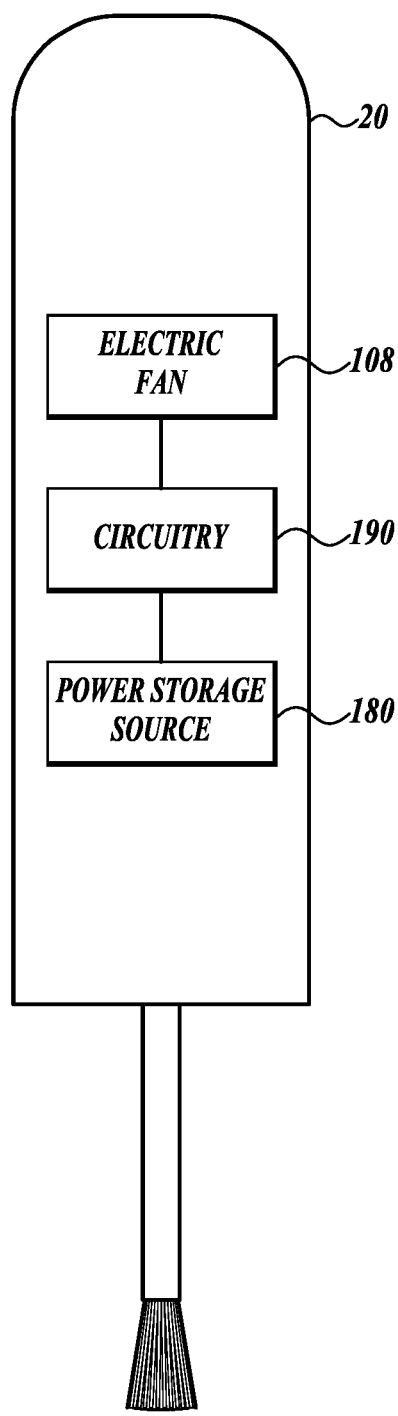
FIG. 10 schematically illustrates the volatile liquid applicator system of FIG. 1.

As shown in FIG. 10, the volatile liquid applicator system 20 may include a power storage source 180, such as a battery, configured to power the electrical fan 108. In an embodiment, the power storage source 180 is a primary battery or a secondary battery. In some embodiments, the power storage source 180 can be a rechargeable battery. In these and other embodiments, suitable power regulation and charging circuitry is provided. It will be appreciated that power requirements for the device will depend on the ultimate function of the device. In some embodiments, wall power can be used to power the electrical fan 108 via a power cord or the like. Further, the volatile liquid applicator system 20 can include circuitry 190 configured to actuate the electrical fan 108.

Turning now to FIG. 2, fumes 120 associated with a volatile liquid applicator 40 are shown. When the electrical fan assembly 100 is in operation, the electrical fan 108 directs fumes 120 associated with the applicator 40 through the one or more passageways 62 of the air flow body 60, across the filter 80, and through the one or more passageways 102 of the electrical motor assembly 100. In so doing, components of the fumes 120 are adsorbed onto or otherwise contained within the filter 80. Accordingly, as air is directed through the system 20 air containing the fumes 120 is purified having a least a portion of the fumes 120 adsorbed onto the filter 80, thereby producing filtered air 122.

As described above, the volatile liquid applicator systems include a filter configured to adsorb or otherwise contain at least a portion of fumes associated with a volatile liquid applicator, when such fumes are moved across the filter. Fumes from volatile liquids, such as those applied with volatile liquid applicators, frequently include volatile organic compounds. Such compounds are often used as solvents and other components of personal care products, such as nail polishes and hair dyes. Accordingly, in an embodiment, the filter is configured to adsorb or otherwise contain a volatile organic compound. In an embodiment, the filter is configured to adsorb or otherwise contain a compound including one or more of ethanol, propanol, isopropanol, ethyl acetate, propyl acetate, butyl acetate, toluene, xylene, formalin, formaldehyde, benzophenone, and dibutylphthalate.

In an embodiment, the filter can include woven, nonwoven, or other mesh materials. Such mesh materials are useful in filtering particulate matter, while still allowing for air flow across the filter. In an embodiment, the filter can include a porous material. Such porous materials advantageously adsorb volatile compounds present in fumes, such as volatile organic compounds. In an embodiment, the filter includes an adsorbent including one or more of activated carbon, potassium permanganate, and zeolites.

In an embodiment, the filter is configured to be removably affixed to the air flow body. In this regard, the filter may be removed and replaced when, for example, the filter is saturated with adsorbed fume components. Similarly, the filter may be removed and replaced if it becomes damaged or is otherwise unsuitable for adsorbing fume components.

Figure 7:
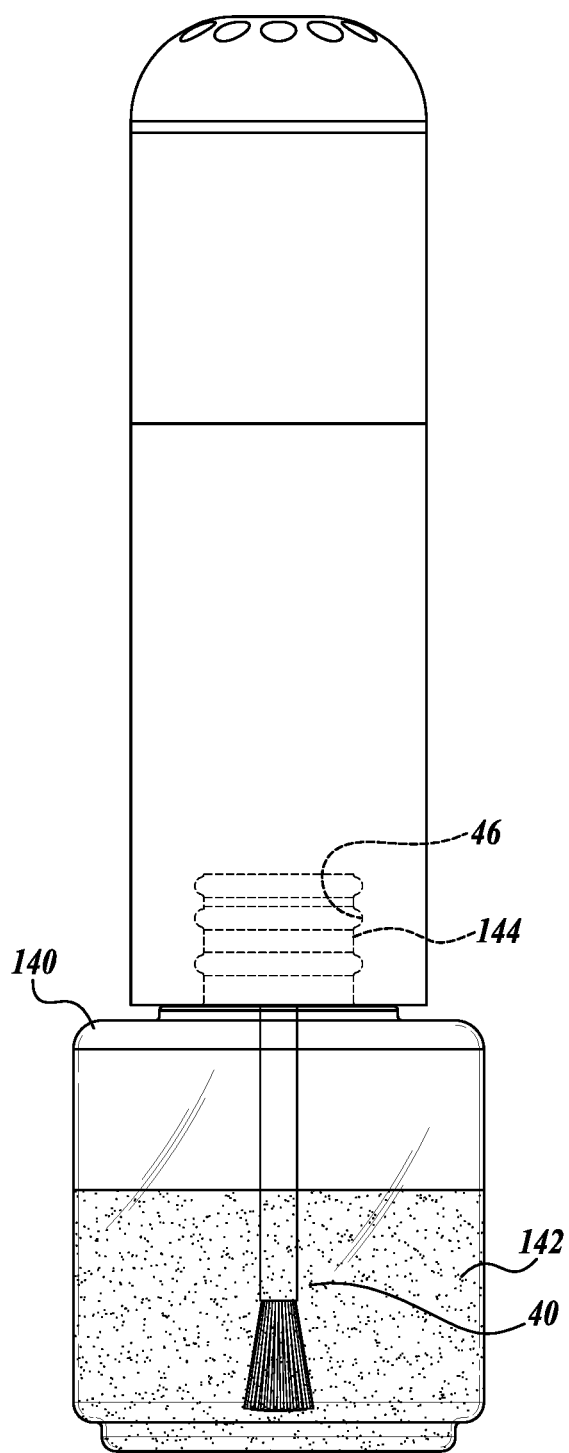
FIG. 7 is front view of a representative embodiment of a volatile liquid applicator system in accordance with an aspect of the disclosure.

In an embodiment, the volatile liquid applicator systems described above may also include a container for containing a volatile liquid. Turning now to FIG. 7, another embodiment of a volatile liquid applicator system is illustrated. The system 20 includes a container 140 for containing a volatile liquid 142. In the embodiment shown, the container 140 is configured so that the volatile liquid applicator 40 is in contact with the volatile liquid 142 so that a user can apply a portion of the volatile liquid 142 to a surface. In an embodiment, the volatile liquid applicator 40 includes a coupling structure configured to couple the container 140 to the volatile liquid applicator 40. In an embodiment, both the container 140 and the volatile liquid applicator 40 include threads 144 and 146, respectively, that are cooperatively configured to couple the container 140 to the volatile liquid applicator 40.

The volatile liquids contained in the containers can be any volatile liquid applied with an applicator. While nail polish is illustrated and described herein, other embodiments provide other volatile liquids, such as hair dye. Volatile liquids include personal care products generally that include volatile components with appreciable vapor pressure. Such volatile personal care liquids include all forms of nail polish including gel, matte, shellac, base coat, and top coat. In an embodiment, the volatile liquid is a hair dye.

In another aspect, the present disclosure provides a fume-filtering apparatus for adsorbing or otherwise containing fumes associated with a volatile liquid applicator. In an embodiment, the fume-filtering apparatus is configured to be coupled to a volatile liquid applicator, such as the applicator 40. As described above, currently available volatile liquid applicators, particularly those for the application of volatile personal care liquids, generate fumes that are dangerous and unpleasant for a user. In some embodiments, the fume-filtering apparatus is configured to be coupled to an existing volatile liquid applicator, such as a cap of a nail polish bottle that includes a brush for applying the nail polish. In this regard, the fume-filtering apparatus can act as an aftermarket filtering device to absorb or otherwise contain fumes associated with an already-existing volatile liquid applicator. In an embodiment, such a fume-filtering apparatus is sold separately from the point-of-sale packaging of a volatile liquid applicator. In an embodiment, such a fume-filtering apparatus is included in the point-of-sale packaging of a volatile liquid applicator.

Figure 8:
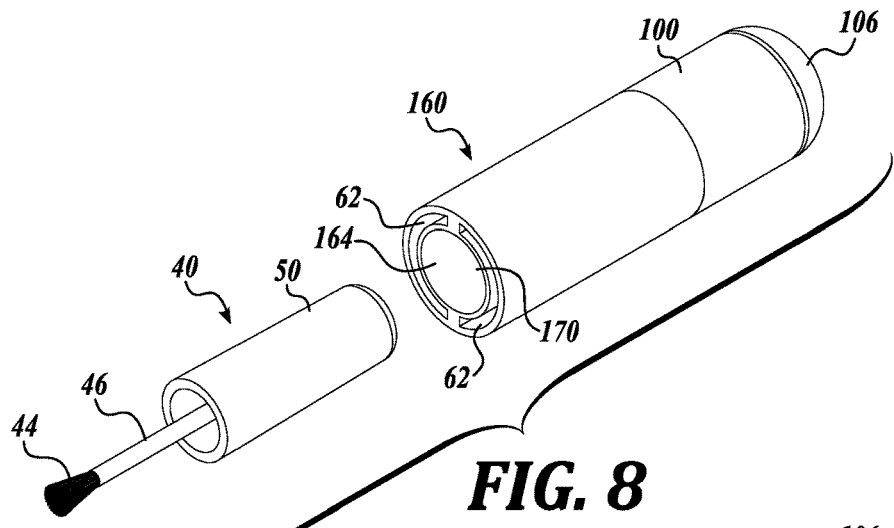
FIG. 8 is a perspective view of a representative embodiment of a fume-filtering apparatus in accordance with an aspect of the disclosure and a volatile liquid applicator.

FIG. 8 illustrates one embodiment of a fume-filtering apparatus, generally designated 160. In the embodiment shown, the fume-filtering apparatus 160 includes the air flow body 60, the filter 80, and the electrical fan assembly 100, described elsewhere herein. In order to provide coupling with an applicator, the fume-filtering apparatus 160 in some embodiments includes a coupling interface 164 configured to couple the handle or cap 42 of a volatile liquid applicator 40 to the air flow body 60 of the fume-filtering apparatus 160.

The air flow body, such as air flow body 60 disclosed herein, is configured to couple with a portion of a volatile liquid applicator, such as the cap of a nail polish applicator. In an embodiment, the air flow body disclosed herein includes a coupling interface configured to couple to a body structure of a volatile liquid applicator 40. In operation, a user can couple the air flow body 60 to the volatile liquid applicator 40 and turn on the electrical fan assembly 100, thereby directing fumes 120 across the filter 80 and adsorb at least a portion of the fumes 120 on to the filter 80.

In an embodiment, the coupling interface 164 is configured to frictionally couple the air flow body 60 to the structure 42. In this regard, the fume-filtering apparatus 160 is configured to be coupled to many currently-available volatile liquid applicators, such as volatile liquid applicator 40, without requiring modification of the volatile liquid applicator. In an embodiment, the coupling interface 164 includes an opening 170 disposed within the air flow body 60 that is configured to receive at least a portion of the volatile liquid applicator 40. As shown, the opening 170 is circular, but may be of any cross-sectional shape in order to accept a portion of volatile liquid applicators of any shape. In this regard, the opening 170 may have a cross-sectional shape selected from circular, square, rectangular, ovoid, triangular, star-shaped, and the like.

In an embodiment, the coupling interface 164 includes an adhesive material disposed on at least a portion of an inner perimeter defined by the opening 170. Such an adhesive material is useful in frictionally coupling the air flow body 60 to the volatile liquid applicator 40 and, in an embodiment, is chosen from silicon rubber, semi-permanent adhesive, removable adhesive, tacky clay, and combinations thereof.

In an embodiment, the coupling interface includes a coupling structure chosen from a snap fit and a snap collar.

Figure 9A:
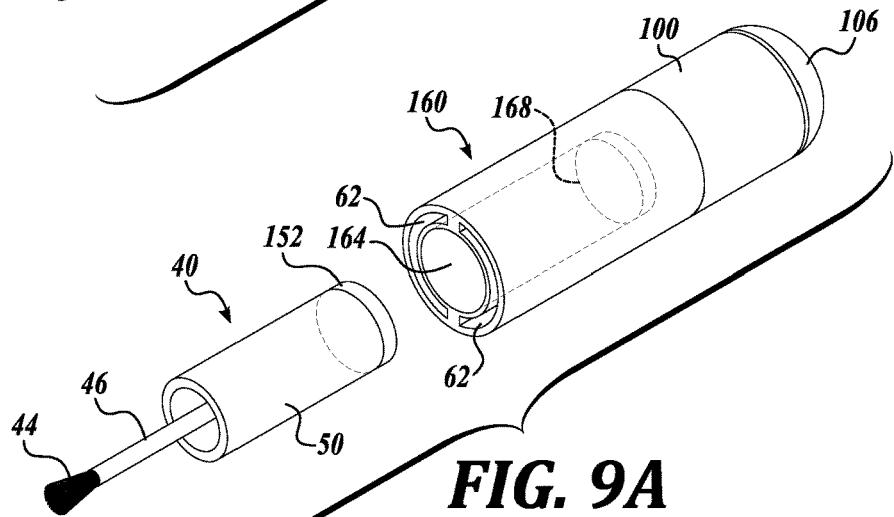
FIG. 9A is a perspective view of a representative embodiment of a fume-filtering apparatus in accordance with an aspect of the disclosure and a volatile liquid applicator.

In another embodiment, the fume-filtering apparatus is configured to be magnetically coupled to a volatile liquid applicator. As shown in FIG. 9A, the coupling interface includes a magnet configured to removably couple the fume-filtering apparatus 160 to a ferromagnetic portion of the volatile liquid applicator. For example, the fume-filtering apparatus 160 includes magnet 168 disposed within the opening 170 configured to receive a portion of the volatile liquid applicator 40. The volatile liquid applicator 40 includes a ferromagnetic portion 152 configured to interact with the magnet 168, thereby magnetically coupling the fume-filtering apparatus 160.

Figure 9B:
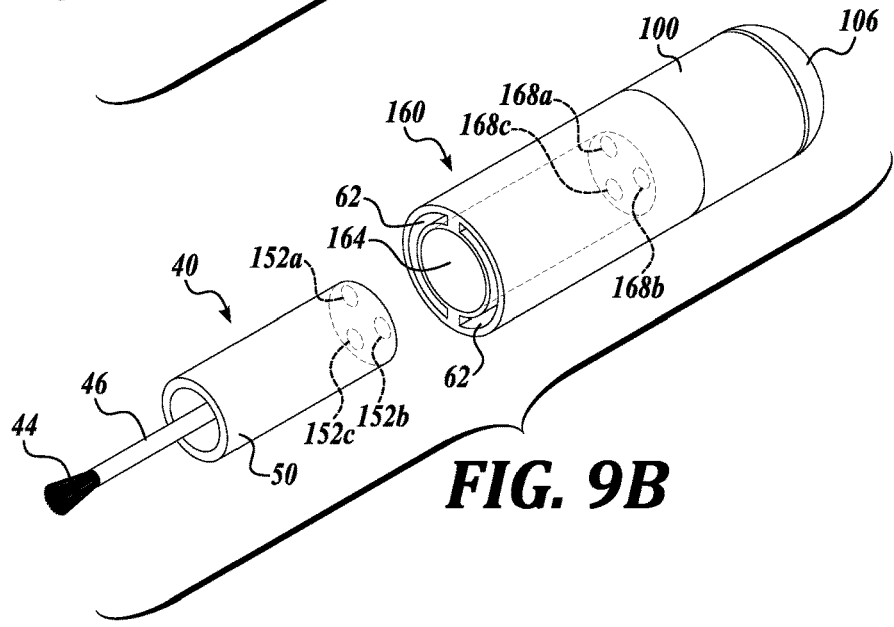
FIG. 9B is a perspective view of a representative embodiment of a fume-filtering apparatus in accordance with an aspect of the disclosure and a volatile liquid applicator.

In an embodiment, the fume-filtering apparatus 160 includes a plurality of magnets configured to interact with a plurality of ferromagnetic portions of the volatile liquid applicator. As shown in FIG. 9B, the fume-filtering apparatus 160 is configured to maintain an orientation about a rotationally-symmetrical axis of the volatile liquid applicator 40. For example, the fume-filtering apparatus 160 includes a plurality of magnets 168a-c disposed in the coupling interface 164. Volatile liquid applicator 40, likewise, includes a plurality of ferromagnetic portions 152a-c corresponding to and configured to interact with the plurality of magnets 168a-c, thereby removably coupling the volatile liquid applicator 40 to the fume-filtering apparatus 160. Further, because each of the plurality of magnets 168a-c interacts with a corresponding ferromagnetic portion 52a-c, the fume-filtering apparatus 160 maintains its orientation about a rotationally-symmetrical axis of the volatile liquid applicator 40. In so doing, the fume-filtering apparatus 160 resists rotation or other motion relative to the volatile liquid applicator 40 when manipulated by a user. Such a feature is advantageous when a user is, for example, applying a volatile liquid, such as nail polish, to a surface and control over the volatile liquid applicator 40 is important to avoid inadvertently applying the volatile liquid to an unintended surface.

Likewise, a fume-filtering apparatus having a non-circular opening configured to accept at least a portion of a volatile liquid applicator that also has a non-circular cross-sectional shape provides a rotational resistance about a rotationally-symmetrical axis of the volatile liquid applicator.

The present application may include references to directions, such as "forward," "rearward," "front," "back," "upward," "downward," "right hand," "left hand," "lateral," "medial," "in," "out," "extended," "advanced," "retracted," "proximal," "distal," "central," etc. These references, and other similar references in the present application, are only to assist in helping describe and understand the particular embodiment and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The terms "about," "approximately," etc., mean plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A volatile liquid applicator system, comprising:
    a body structure including a volatile liquid applicator and an air flow body including a filter; and
    an electrical fan assembly associated with the air flow body, the electrical fan assembly configured to direct fumes associated with a volatile liquid away from a portion of the volatile liquid applicator and across the air filter,
    wherein the air flow body includes a passageway extending through a portion of the air flow body from a position adjacent to the volatile liquid applicator to a position adjacent to the filter and configured to allow passage of the fumes associated with the volatile liquid applicator through the air flow body and across the filter.

2. The volatile liquid applicator system of claim 1, wherein the air flow body is configured to assist in drying based on redirecting air direction.

3. The volatile liquid applicator system of claim 1, wherein the passageway is one of a plurality of passageways configured to allow passage of the fumes associated with the volatile liquid applicator through the air flow body and across the filter.

4. The volatile liquid applicator system of claim 1, wherein the electrical fan assembly includes a fan structure selected from the group consisting of an inductive fan, an axial-flow fan, a centrifugal fan, a cross-flow fan, and combinations thereof.

5. The volatile liquid applicator system of claim 1, wherein the filter is configured to absorb a volatile organic compound.

6. The volatile liquid applicator system of claim 1, wherein the filter is configured to adsorb a compound selected from the group consisting of ethanol, propanol, isopropanol, ethyl acetate, propyl acetate, butyl acetate, toluene, xylene, formalin, formaldehyde, benzophenone, dibutylphthalate, and combinations thereof.

7. The volatile liquid applicator system of claim 1, wherein the filter includes an adsorbent selected from the group consisting of activated carbon, potassium permanganate, zeolites, and combinations thereof.

8. The volatile liquid applicator system of claim 1, wherein the filter is configured to be removably affixed to the air flow body.

9. The volatile liquid applicator system of claim 1, further comprising a container for containing a volatile liquid, wherein the container is configured to removably couple with the body structure.

10. The volatile liquid applicator system of claim 9, wherein the container for containing a volatile liquid includes a volatile liquid.

11. The volatile liquid applicator system of claim 9, wherein the volatile liquid is selected from the group consisting of nail polish, hair dye, and combinations thereof.

12. A fume-filtering apparatus comprising:

an air flow body including a filter, the air flow body configured to couple with a body structure of a volatile liquid applicator; and an electrical fan assembly associated with the air flow body, the electrical fan assembly configured to direct fumes associated with a volatile liquid away from a portion of the volatile liquid applicator and across the filter, wherein the air flow body includes a passageway extending through a portion of the air flow body from a position adjacent to the volatile liquid applicator to a position adjacent to the filter and configured to allow passage of the fumes associated with the volatile liquid applicator through the air flow body and across the filter.

13. The fume-filtering apparatus of claim 12, wherein the air flow body is configured to assist in drying based on redirecting air direction.

14. The fume-filtering apparatus of claim 12, further comprising a coupling interface configured to couple the body structure to the air flow body.

15. The fume-filtering apparatus of claim 14, wherein the coupling interface includes a magnet configured to couple the air flow body to a ferromagnetic portion of the body structure.

16. The fume-filtering apparatus of claim 15, wherein the magnet is one of a plurality of magnets, and wherein the air flow body is configured to maintain an orientation about a rotationally-symmetrical axis of the body structure.

17. The fume-filtering apparatus of claim 14, wherein the coupling interface is configured to frictionally couple the air flow body to the body structure.

18. The fume-filtering apparatus of claim 14, wherein the coupling interface includes an opening in the air flow body configured to receive at least a portion of the volatile liquid applicator, and wherein the coupling interface includes an adhesive material selected from the group consisting of silicon rubber, semi-permanent adhesive, removable adhesive, tacky clay, and combinations thereof disposed on at least a portion of an inner perimeter defined by the opening.

19. The fume-filtering apparatus of claim 14, wherein the coupling interface includes a coupling structure selected from the group consisting of a snap fit, a snap collar, and combinations thereof.

* * * * *